US011710537B2

(12) United States Patent
Hua et al.

(10) Patent No.: US 11,710,537 B2
(45) Date of Patent: Jul. 25, 2023

(54) OPTIMAL SELECTION METHOD OF GENE CHIP PROBES FOR CANCER SCREENING

(71) Applicant: BEIJING BIONAXIN BIOTECH CO., LTD, Beijing (CN)

(72) Inventors: Ziang Hua, Beijing (CN); Baoquan Liu, Beijing (CN); Tian Zhu, Beijing (CN); Meiying Zhu, Beijing (CN); Junxing Wan, Beijing (CN); Jian Zhang, Beijing (CN); Na Li, Beijing (CN)

(73) Assignee: BEIJING BIONAXIN BIOTECH CO., LTD, Beijing (CN)

( * ) Notice: Subject to any disclaimer, the term of this patent is extended or adjusted under 35 U.S.C. 154(b) by 0 days.

(21) Appl. No.: 17/578,498

(22) Filed: Jan. 19, 2022

(65) Prior Publication Data
US 2022/0246237 A1 Aug. 4, 2022

(30) Foreign Application Priority Data

Feb. 1, 2021 (CN) .......................... 202110133481.3

(51) Int. Cl.
*G16B 25/20* (2019.01)
*C12Q 1/6811* (2018.01)
*C12Q 1/6886* (2018.01)

(52) U.S. Cl.
CPC ............ *G16B 25/20* (2019.02); *C12Q 1/6811* (2013.01); *C12Q 1/6886* (2013.01); *C12Q 2600/156* (2013.01)

(58) Field of Classification Search
CPC ........ G16B 25/20; G16B 20/30; G16B 20/50; G16B 25/30; C12Q 1/6811; C12Q 1/6886; C12Q 1/681; C12Q 2600/156
See application file for complete search history.

(56) References Cited

U.S. PATENT DOCUMENTS

| | | | | |
|---|---|---|---|---|
| 2012/0157322 A1* | 6/2012 | Myllykangas | ....... | C12Q 1/6806 435/91.2 |
| 2014/0200146 A1* | 7/2014 | Xie | .................... | C12N 15/1093 506/26 |

FOREIGN PATENT DOCUMENTS

| | | |
|---|---|---|
| CN | 101363046 A | 2/2009 |
| CN | 110066876 A | 7/2013 |
| CN | 106566877 A | 4/2017 |
| CN | 111647648 A | 9/2020 |
| KR | 20200004977 A | 1/2020 |
| WO | 2015180489 A1 | 12/2015 |

\* cited by examiner

*Primary Examiner* — Jeremy C Flinders

(57) ABSTRACT

The invention relates to an optimal selection method of gene chip probes for cancer screening. The method is characterized in that the gene chip probes capable of being used for cancer screening are obtained through three stages of constructing a point mutation site (SNV) group, constructing a candidate probe group and verifying and confirming probes on the basis of nucleic acid data of a confirmed case of a selected cancer.

4 Claims, No Drawings
Specification includes a Sequence Listing.

OPTIMAL SELECTION METHOD OF GENE CHIP PROBES FOR CANCER SCREENING

STATEMENT REGARDING SEQUENCE LISTING

The Sequence Listing associated with this application is part of the application and is provided in text in the form of an ASCII text file in lieu of a paper copy, and is hereby incorporated by reference into the specification. The name of the Sequence listing is—SEQUENCE LISTING.txt.—The text file is 824 bytes in size, was created on Apr. 1, 2022, and is being electronically submitted via EFS-Web.

FIELD OF THE INVENTION

The invention relates to biochip field, especially to an optimal selection method of gene chip probes for cancer screening.

DESCRIPTION OF THE BACKGROUND ART

Biochip technology has been widely used in many fields, such as clinical disease diagnosis, health management, drug research and development, animal and plant quarantine, food detection, environmental monitoring, scientific research, forensic detection. Biochip shows a considerable promise and great market demand.

Gene chip is a kind of biochip. It is prepared by planting a series of probes of known sequences on a substrate of a chip. It can be used for hybridization detection of specifically labeled nucleic acids. It can report the nucleic acid information in the detection object through identification, detection and information processing.

The key technology of gene chip manufacturing is how to effectively obtain specific probes of a gene chip. Only by obtaining the specific probes can we design and produce gene chips. The technology of obtaining gene chip probes has become a core of competition in the field of gene chip industry.

At present, the technology for designing and optimizing gene chip probes is mainly in the hands of several large foreign companies, and a series of cancer drug screening chips have been developed. However, there is no cancer screening gene chips for Chinese population in the market, and developing such chips will not only be a great contribution to the protection of national gene resources, but is also a great challenge to the development of gene chip technology in China. We must establish our own manufacturing line of cancer screening gene chips, while designing gene chip probes is a top priority.

SUMMARY OF THE INVENTION

In order to solve the shortcomings of the prior art, the invention provides an optimal selection method of obtaining gene chip probes for cancer screening through three stages of constructing a point mutation site (SNV) group, constructing a candidate probe group and verifying and confirming probes. The optimized gene chip probes may be used for preparing gene chip on cancer screening.

The concept of the invention is that cancer is caused by incontrollable proliferation of cells, wherein cells proliferation roots directly in DNA and DNA is the fundamental cause. There are sequence changes of DNAs in the nucleic acid detection data of confirmed cancer cases, therefore, a gene chip could be prepared to screen cancer if specific probes for cancer is screened out and obtained, and then making it possible to effectively prevent cancer deterioration by interventions in the early development stages of the cancer.

In order to solve the above problems, the invention provides a technical solution called an optimal selection method of gene chip probes for cancer screening comprising the following steps:

S1 Selecting a cancer as the screening target and obtaining nucleic acid detection data of confirmed cases of the cancer;

S2 Determining corresponding SNV sites and constructing a SNV group by sequence alignment between the nucleic acid detection data of the confirmed cases of the cancer and human genome big data;

S3 With each point mutation site of the point mutation site group as a center, conducting sequence extension and sequence alignment to select candidate probes of the point mutation sites and construct a candidate probe group;

S4 Verifying and confirming the probes by preparing a test chip by using sequence information of the candidate probes of the candidate probe group, then screening out the candidate probes that their positive detection results are consistent with the confirmed cancer cases, which are the gene probes capable of being used for cancer screening.

Preferably, the gene chip probes are obtained through three stages of constructing a SNV group, constructing a candidate probe group, and verifying and confirming probes.

Preferably, the SNV sites and corresponding functional annotations of the SNV sites are obtained by sequence alignment between the nucleic acid detection data of the confirmed cases of the cancer and human genome big data.

Preferably, the functional annotations of the SNV sites include functional annotations of genes where the SNV sites are located and the functional annotations of the chromosome segments where the SNV sites are located.

Preferably, the candidate probes are obtained through the combination of sequence proliferation and sequence alignment with the SNV sites as a core.

Preferably, the candidate probes have a length of 15-25 nucleotides and the number of base pairings is 5-10 for the longest base pairings in succession between the candidate probes and the genome sequence other than the genome sequence itself.

Preferably, a validation criterion for verifying the probes is a confirmed diagnosis result of the cancer by a hospital.

Preferably, the sequencing data of single cells is used to conduct selection of the gene chip probes for cancer screening, and the sequencing data of single cells may come from but is not limited to the urine exfoliated cells, menstrual blood cells, cells got by puncturing, exfoliated cells from different parts of the body, blood or tissue fluid from a cancer patient.

The invention has more merits than the prior art including the established three tightly connected stages of constructing a SNV group, constructing a candidate probe group and verifying and confirming probes, which make us capable of correlating a specific gene chip probes with specific cancer screening, and eventually make it possible to screen out cancers in the early stages and to further reduce the progress of cancer by early intervention.

DETAILED DESCRIPTION OF THE INVENTION

The invention will be further explained in details by the following embodiments. The following embodiments are only description instead of defining, and shall not be used to define the protection scope of the invention. All chemical reagents and apparatus used in the embodiments can be commercially purchased unless otherwise specified.

Embodiment 1: An Optimal Selection Method of Gene Chip Probes for Breast Cancer Screening Development of gene chip probes for screening breast cancer was conducted by cooperation with a cancer hospital (First-class Hospital at Grade 3) or an oncology department, wherein whole genome sequencing was made on the faulty tissues of the confirmed breast cancer patients to obtain the nucleic acid detection data of the breast cancerous tissues (cells).

As sequence alignment between the nucleic acid detection data of the breast cancerous tissues (cells) and human genome database (e.g., NCBI-GeneBank and etc.) was made together with reference to SNV database (e.g., NCBI-Clinvar and etc.), corresponding SNV sites of the breast cancerous tissues (cells) were identified. For example, a SNV mutation in base conversion of G>A was found in the nucleic acid detection data of the breast cancerous tissues (cells), the same SNV mutation was also found in the database of NCBI-Clinvar (r5786205165, NM 004958.4: c.4448G>A, functional annotation (>ref|NM_004958.4|: 4419-4465*Homo sapiens* mechanistic target of rapamycin kinase (MTOR), transcript variant 1, mRNA). The functional annotation explained that the occurrence of the base conversion made the alteration of cysteine into tyrosine in protein. All the detected SNV sites were gathered to form the SNV group.

Taking each SNV site in the SNV group as the core, those sequences of 15-20 nucleotides in length were captured for sequence alignment between the human genome database and the nucleic acid detection data of breast cancerous tissues (cells) to screen out sequences that have 5-10 base pairings in succession as candidate probes; and the candidate probe group was established by gathering all the candidate probes; wherein comprising the candidate probe based on SNV mutation (r5786205165): GAGAGCTGGAGATCCAG (SEQ ID NO: 1).

The candidate probes in the candidate probe group were compared and analyzed by taking advantage of the nucleic acid detection data of the breast cancerous tissues (cells) of the confirmed cases, which was called probes verification; the breast cancer probes capable of preparing gene chips could be selected from the candidate probe group by verifying the probes; wherein comprising the SNV mutation (r5786205165) probe:

GAGAGCTGGAGATCCAG. (SEQ ID NO: 2)

Embodiment 2: An Optimal Selection Method of Gene Chip Probes for Lung Cancer Screening Development of gene chip probes for screening lung cancer was conducted by cooperation with a cancer hospital (First-class Hospital at Grade 3) or an oncology department, whole genome sequencing was made on the faulty tissues of confirmed lung cancer patients to obtain the nucleic acid detection data of the lung cancer tissues (cells).

As sequence alignment between the nucleic acid detection data of the lung cancer (cells) and human genome database (e.g., NCBI-GeneBank and etc.) was made together with reference to SNV database (e.g., NCBI-Clinvar and etc.), corresponding SNVs of the lung cancer (cells) were identified. For example, a SNV of deletion mutation was found in the nucleic acid detection data of the lung cancerous tissues (cells), the same SNV mutation was also found in the database of NCBI-Clinvar (rs587779846, NM_001351834.2:c.5290del, (*Homo sapiens* ATM serine/threonine kinase (ATM), transcript variant 1, mRNA). Functional annotations explained that the occurrence of the base deletion led to the result that only truncated protein was produced in the protein translation, which further impacted the activation of regulatory proteins including p53 and BRCA1, resulting in the occurrence of a cancer. All the detected SNVs were gathered to form the SNV group.

Taking each SNV site in the SNV group as the core, those sequences of 15-20 nucleotides in length were captured for sequence alignment between the human genome database and the nucleic acid detection data of lung cancerous tissues (cells) to screen out sequences that have 5-10 base pairings in succession as candidate probes. Then a candidate probe group was established by gathering all the candidate probes, wherein comprising the candidate probe based on SNV site (r5587779846): gctggcctattacagcctt (SEQ ID NO: 3).

The candidate probes in the candidate probe group were compared and analyzed by taking advantage of the nucleic acid detection data of the lung cancerous tissues (cells) of the confirmed cases, which was called probes verification; the lung cancer probes capable of preparing gene chips could be selected from the candidate probe group through the probe verification, wherein comprising the SNV (rs587779846) probe: gctggcctattacagcctt (SEQ ID NO: 4).

The abovementioned embodiments are only preferred embodiments of the invention; however, the protection scope of the invention shall not be limited by the embodiments, all equivalent replacements or modifications made according to the technical solutions or conceptions of the invention by any person skilled in the art within the technical range disclosed by the invention, shall be covered by the protection of the invention.

What is claimed is:

1. An optimal selection method of gene chip probes for cancer screening comprising the following steps:
   S1 Selecting a cancer as the screening target and obtaining nucleic acid data of confirmed cases of the cancer;
   S2 Determining corresponding point mutation sites and constructing a point mutation site group by sequence alignment between the nucleic acid data of the confirmed cases of the cancer and human genome data;
   S3 With each point mutation site of the point mutation site group as a center, conducting sequence extension and sequence alignment to select candidate probes of the point mutation sites and construct a candidate probe group;
   S4 Verifying the probes by preparing a test chip by using sequence information of the candidate probes of the candidate probe group, then selecting the candidate probes of the test chip that have positive detection results consistent with confirmed cancer cases, wherein a validation criterion for verifying the probes is a confirmed diagnosis result of the cancer by a hospital from cancer cases, wherein the sequencing data of single cells is used to conduct selection of the gene chip probes for cancer screening and detecting, which selected candidate probes are gene probes capable of being used for cancer screening and detecting.

2. The optimal selection method of gene chip probes for cancer screening as claimed in claim 1, wherein the sequence alignment between the nucleic acid data of confirmed cancer cases of a cancer and the human genome data of S2 to determine the point mutation sites further comprises obtaining the corresponding functional annotations of the point mutation sites.

3. The optimal selection method of gene chip probes for cancer screening as claimed in claim 2, wherein the functional annotations of the point mutation sites include functional annotations of the genes where the point mutation sites are located and functional annotations of the chromosome segments where the point mutation sites are located.

4. The optimal selection method of gene chip probes for cancer screening as claimed in claim 1, wherein the sequencing data of single cells is from cancer patient's urine exfoliated cells, menstrual blood cells, cells obtained by puncturing, exfoliated cells from different parts of the body, blood or tissue fluid.

* * * * *

SEQUENCE LISTING

<160> NUMBER OF SEQ ID NOS: 4

<210> SEQ ID NO 1
<211> LENGTH: 17
<212> TYPE: DNA
<213> ORGANISM: Homo sapiens

<400> SEQUENCE: 1
gagagctgga gatccag                                          17

```
<210> SEQ ID NO 2
<211> LENGTH: 17
<212> TYPE: DNA
<213> ORGANISM: Homo sapiens

<400> SEQUENCE: 2
gagagctgga gatccag                                                  17

<210> SEQ ID NO 3
<211> LENGTH: 19
<212> TYPE: DNA
<213> ORGANISM: Homo sapiens

<400> SEQUENCE: 3
gctggcctat tacagcctt                                                19

<210> SEQ ID NO 4
<211> LENGTH: 19
<212> TYPE: DNA
<213> ORGANISM: Homo sapiens

<400> SEQUENCE: 4
gctggcctat tacagcctt                                                19
```